United States Patent [19]

Montgomery

[11] 4,329,494

[45] May 11, 1982

[54] RECYCLING TECHNIQUES IN THE PRODUCTION OF 6-HYDROXY-2-NAPHTHOIC ACID

[75] Inventor: Carroll S. Montgomery, Somerville, N.J.

[73] Assignee: American Cyanamid Company, Stamford, Conn.

[21] Appl. No.: 285,728

[22] Filed: Jul. 22, 1981

[51] Int. Cl.³ .............................................. C07C 51/15
[52] U.S. Cl. ..................................................... 562/425
[58] Field of Search ................................. 562/425, 423

[56] References Cited

U.S. PATENT DOCUMENTS

| | | | |
|---|---|---|---|
| 1,470,039 | 10/1925 | Wallach | 562/425 |
| 1,648,839 | 11/1927 | Calcott et al. | 562/425 |
| 1,700,546 | 1/1929 | Schwenk | 562/425 |
| 2,132,356 | 10/1938 | Lecher et al. | 562/425 |
| 2,544,881 | 3/1951 | Hodges et al. | 562/425 |
| 4,239,913 | 12/1980 | Ueno et al. | 562/425 |

FOREIGN PATENT DOCUMENTS

| | | | |
|---|---|---|---|
| 31240 | 9/1884 | Fed. Rep. of Germany | 562/425 |
| 120257 | 5/1927 | Switzerland | 562/425 |

*Primary Examiner*—Paul J. Killos
*Attorney, Agent, or Firm*—Bruce F. Jacobs

[57] ABSTRACT

The production of 6-hydroxy-2-naphthoic acid from anhydrous potassium 2-naphthoxide and carbon dioxide is improved by introducing 3-hydroxy-2-naphthoic acid to the initial stages of the process.

5 Claims, No Drawings

RECYCLING TECHNIQUES IN THE PRODUCTION OF 6-HYDROXY-2-NAPHTHOIC ACID

The present invention relates to a process for the preparation of 6-hydroxy-2-naphthoic acid by the carboxylation of the potassium salt of 2-hydroxynaphthalene with carbon dioxide in which said potassium salt is reacted with carbon dioxide under specific conditions of temperature, pressure, and ratios of reactants, and the 6-hydroxy-2-naphthoic acid is recovered wherein 3-hydroxy-2-naphthoic acid is introduced into the initial stage of the process.

BACKGROUND OF THE INVENTION

The production of 6-hydroxy-2-naphthoic acid, an intermediate useful for the preparation of synthetic fibers, and structural plastics, by the reaction of the potassium salt of 2-hydroxynaphthalene and carbon dioxide at an elevated temperature, is disclosed by Andre in U.S. Pat. No. 1,593,816. Andre, however, does not disclose the criticality of temperature, pressure, or ratios of reactants. Moreover, upon repeating Andre's work, the actual yield of 6-hydroxy-2-naphthoic acid obtained was found to be only about one-third of the yield reported by Andre. Additionally, an improved process is disclosed and claimed in pending application Ser. No. 127,703, filed Mar. 6, 1980, now U.S. Pat. No. 4,287,357 herebyincorporated herein by reference.

The carboxylation of alkali metal salts of phenols with carbon dioxide to form acids containing phenolic substituents, the well-known Kolbe-Schmitt reaction, is also disclosed in U.S. Pat. Nos. 3,816,521 and 3,405,169.

In the carboxylation of the potassium salt of 2-hydroxynaphthalene, the initial product formed is 3-hydroxy-2-naphthoic acid which subsequently rearranges in situ to form 6-hydroxy-2-naphthoic acid. This rearrangement is rapid until the ratio of 6-hydroxy-2-naphthoic acid to 6-hydroxy-2-naphthoic acid plus 3-hydroxy-2-naphthoic acid is approximately about 0.6–0.8 and the rearrangement is slow up to the equilibrium ratio of about 0.9–0.93. This slow rearrangement requires a long reaction time which leads to undesirable tar formation and, accordingly, lost yield, increased energy use and increased cost. The 3-hydroxy-2-naphthoic acid which is capable of recovery from the equilibrium product is contaminated with small quantities of 6-hydroxy-2-naphthoic acid and 2-naphthol dicarboxylic acid. It is of poor quality without extremely expensive reworking thereof and is thereforegenerally discarded.

There is need, therefore, for an improved process for the production of 6-hydroxy-2-naphthoic acid which will enable lower reaction times, increased yields based on 2-hydroxy naphthalene and reduced amounts of process residue, which, if discarded, must be done so in a non-polluting manner.

SUMMARY OF THE INVENTION

In accordance with the present invention, there is provided a process for preparing 6-hydroxy-2-naphthoic acid by (A) forming a mixture of 2-hydroxy naphthalene and potassium base, (B) dehydrating the resultant mixture, (C) introducing carbon dioxide into the resultant deydrated mixture while agitating under heat and pressure and (D) recovering the resultant 6-hydroxy-2-naphthoic acid, wherein (E) the mixture is heated during agitation at a temperature of about 270°–280° C. and at a pressure of about 68–74 psi until the ratio of 6-hydroxy-2-naphthoic acid to the mixture of 6-hydroxy-2-naphthoic acid plus 3-hydroxy-2-naphthoic acid therein is at least about 0.4 and (F) 3-hydroxy-2-naphthoic acid is introduced to the initial stages of the process.

The improved process of the present invention affords the following advantages:

1. A higher yield of 6-hydroxy-2-naphthoic acid based on 2-naphthol is obtained, said 2-naphthol being the most costly raw material on a mole basis used in the process.

2. A higher productivity in the manufacture of 6-hydroxy-2-naphthoic acid is achieved.

3. A greatly reduced amount of process residue is produced.

DESCRIPTION OF THE INVENTION

In carrying out the process over which the present invention is an improvement, 2-hydroxynaphthalene and a potassium base are mixed in amounts sufficient to provide a ratio of about 0.8 to 1.45 moles of 2-hydroxynaphthalene per equivalent of potassium base, and the reaction mixture is dehydrated by distillation, or by passing it through a dehydration apparatus.

Suitable useful potassium bases include potassium hydroxide, potassium carbonate, potassium hydride, potassium amide, and the like, as well as mixtures thereof. The preferred potassium base is potassium hydroxide alone or in admixture with potassium carbonate.

Preferably, the potassium base and 2-hydroxynaphthalene are mixed in the presence of a non-polar organic flux to form the potassium 2-naphthoxide and the reaction mixture is dehydrated by distillation under nitrogen until essentially all of the water is removed.

Preferably, in forming the reaction mixture about 1.0 to 1.1 moles of 2-hydroxynaphthalene, and most preferably, about 1.02 to 1.04 moles, are used per mole of potassium base. A large excess of 2-hydroxynaphthalene, for example, above about 1.5 moles per mole of potassium hydroxide, has been found to produce a large decrease in the yield of the final product.

As used herein, the term "flux" is defined as any non-polar organic material which is not a solvent for the reactants and which is a liquid under the reaction conditions employed. Suitable materials which may be used as a flux include the following:

1-isopropylnaphthalene,
2-isopropylnaphthalene,
naphthalene,
kerosene, and the like.

The preferred flux is a mixture of 1-, and 2-isopropylnaphthalene. Preferably, the dehydrated mixture contains about one part by weight of potassium 2-naphthoxide per part by weight of the mixed isopropylnaphthalenes.

In accordance with the first feature of the novel improvements of the process according to the instant invention, 3-hydroxy-2-naphthoic acid is introduced into either the stage of the process herein the potassium base and the 2-hydroxy-naphthalene are admixed or into the dehydration stage. When the 3-hydroxy-2-naphthoic acid is introduced into the mixing stage, no more than about a 50/50 molar ratio with the 2-hydroxnaphthalene should be used. Preferably, from about 5–30 parts of 3-hydroxy-2-naphthoic acid per 100 parts of 2-hydroxynaphthalene have been found effective.

When the 3-hydroxy-2-naphthoic acid is added to the dehydration stage it must first be contacted with potassium base in order to convert substantially all the hydroxy and carboxy groups to potassium salts. The amount of hydroxy-2-naphthoic acid added to the dehydration stage is, however, still within the concentration discussed above with respect to the mixing stage.

Once the mixture is dehydrated, it is then charged to a pressure reactor, preferably with additional flux and purged with carbon dioxide. The reactor is then sealed and heated, according to the second feature of the present improvement, at a temperature ranging from about 270° C. to 280° C., under a carbon dioxide pressure of ranging from about 68–74 psi, while stirring the reaction mixture vigorously. The reaction is continued until analysis of an aliquot of the reaction mixture shows a ratio of 6-hydroxy-2-naphthoic acid to the mixture of 6-hydroxy-2-naphthoic acid and 3-hydroxy-2-naphthoic acid of at least about 0.4, preferably from about 0.6–0.9, and, most preferably, from about 0.7–0.8. The agitation must be sufficient to ensure the uniform mixing of the carbon dioxide into the reaction mixture, otherwise the carboxylation reaction stops.

When the ratio set forth above is reached, the reactor is vented to the atmosphere and the reaction mixture is cooled under a nitrogen atmosphere to about 120° C. The reaction mixture is then either diluted with water and/or discharged into water containing enough sulfuric acid to bring the pH of the resulting mixture to 7, or above, preferably about 7.1±0.2.

The aqueous phase of the resulting two-phase liquid mixture is split off from the organic phase at a temperature of about 85°–98° C., preferably about 95° C., and is back-extracted twice with an equal volume of an organic flux (even if the flux was not present during the reaction) at the same temperature as the aqueous phase. A buffer, preferably about 0.1 gram of acetic acid per gram of 6-hydroxy-2-naphthoic acid expected, is added to the extracted aqueous phase, and then enough dilute sulfuric acid to adjust the pH to about 4.8 to 5.2 to precipitate the 6-hydroxy-2-naphthoic acid. The precipitate may then be recovered by conventional means and dried to obtain the desired 6-hydroxy-2-naphthoic acid in a yield of about 40–60% of theoretical.

In accordance with a further feature of the present invention, the mother liquor obtained on recovery of the 6-hydroxy-2-naphthoic acid is treated to recover a stream rich in 3-hydrox-2-naphthoic acid which is generally a mixture of 3-hydroxy-2-naphthoic acid; 6-hydroxy-2-naphthoic acid and 2-naphthol dicarboxylic acid. This treatment is effected by adjusting the pH of the mother liquor to about 2.5 such as with dilute sulfuric acid, filtering the resultant material and washing to recover the desired mixture as a wet cake. Optionally, the cake may be dried if desired.

The recovered mixture, rich in 3-hydroxy-2-naphthoic acid, is then recycled to the initial steps of the process as the 3-hydroxy-2-naphthoic acid component discussed above. That is to say, according to an improvement of the present invention, the 3-hydroxy-2-naphthoic acid rich mixture is either (1) recycled directly to the stage of the process where the 2-hydroxynaphthalene is contacted with the potassium base or (2) recycled directly to the dehydration stage after contact with potassium base. Sufficient potassium base is employed in this latter instance so as to form the potassium salts of the hydroxy and carboxy groups of the 3-hydroxy-2-naphthoic acid rich mixture. The reaction is then continued as described above.

Alternatively, the 3-hydroxy-2-naphthoic rich mixture can be admixed with a portion of extraneously produced 3-hydroxy-2-naphthoic acid, and then added either to the mixing stage or the dehydration stage. That is to say, the improvement of the present invention includes (1) the use of pure 3-hydroxy-2-naphthoic acid produced extraneously added to the process, (2) the use of the 3-hydroxy-2-naphthoic acid-rich recycle stream or (3) mixtures of the extraneous stream and the recycle stream.

In the examples which follow, all parts are by weight unless otherwise indicated. All yields are based on potassium base charged. A theoretical yield is defined as one mole of 6-hydroxy-2-naphthoic acid produced for every 2 moles of potassium 2-naphthoxide.

EXAMPLE 1

(Comparative)

A mixture of 2-hydroxynaphthalene (84 grams; 0.58 mole), 45% potassium hydroxide (70.5 grams; 0.56 mole), and 100 mls of a mixture of 1-, and 2-isopropyl-naphthalenes is stirred and heated under a nitrogen atmosphere until 100 mls total of water and isopropylnaphthalene are distilled off. At that point, 100 mls of isopropylnaphthalene is added and the mixture is further heated to distill off an additional 50 mls of isopropylnaphthalene, and obtain a dehydrated mixture.

The dehydrated reaction mixture is cooled to 65° C., charged to a pressure reactor, and purged with carbon dioxide. The reactor is then sealed and pressurized with carbon dioxide to 70 psi while stirring slowly. The rate of stirring is then increased to 1500 rpm and the mixture is stirred at 275° C. under 70 psi of carbon dioxide for 4 hours. The reaction mixture is then cooled to 240° C., vented to atmospheric pressure, and cooled under a nitrogen atmosphere to 120° C. Water is then added to dilute the reaction mixture.

The diluted reaction mixture is discharged into a flask containing 7.5 grams of sulfuric acid in 100 mls of water. The pH of the resulting mixture is then adjusted to 7.0±1 with sulfuric acid, and the two-phase liquid mixture is heated to 95° C. while stirring. The mixture is allowed to settle, the layers are split apart, and the aqueous phase is washed twice with 100-ml portions of isopropylnaphthalene. The isopropylnaphthalene-washed aqueous phase is then stirred at 65°–75° C. and 20 grams of a 15% by weight solution of acetic acid in water is added thereto. Sulfuric acid (15 grams of sulfuric acid per 100 mls of solution) is then added over a period of 15 to 30 minutes until the pH of the resulting slurry is 4.8 to 5.2. The slurry is then cooled to 25°–35° C. and filtered. The resulting filter cake is then washed with water and dried to obtain 21.7 grams of 6-hydroxy-2-naphthic acid.

The aqueous mother liquor is adjusted to pH 2.5 with dilute sulfuric acid and the resulting precipitate is collected by filtration, washed, and dried to afford a 3-hydroxy-2-naphthoic acid-rich stream containing 2-naphthol dicarboxylic acid; 6-hydroxy-2-naphthoic acid and 3-hydroxy-2-naphthoic acid, wt. 6.6 g.

The combined organic phases contain 53.9 grams of 2-hydroxynaphthalene, which can be recovered and recycled. This result is equivalent to a 42.9% yield based on KOH and 55.2% yield on 2-naphthol.

EXAMPLE 2

A mixture of 2-hydroxynaphthalene (84 grams; 0.58 mole), 45% potassium hydroxide (78.4 grams; 0.62 mole), the 6.6 g of 3-hydroxy-2-naphthoic acid-rich mixture produced in Example 1, above, and 100 mls of a mixture of 1-, and 2-isopropylnaphthalenes is stirred and heated under a nitrogen atmposphere until 100 mls total of water and isopropylnaphthalene are distilled off. At that point, 100 mls of isopropylnaphthalene is added and the mixture is further heated to distill off an additional 50 mls of isopropylnaphthalene, and obtain a dehydrated mixture.

The dehydrated reaction mixture is cooled to 265° C., charged to a pressure reactor, and purged with carbon dioxide. The reactor is then sealed and pressurized with carbon dioxide to 70 psi while stirring slowly. The rate of stirring is then increased to 1500 rpm and the mixture is stirred at 275° C. under 70 psi of carbon dioxide for 4 hours, until the ratio of 6-hydroxy-2-naphthoic acid to the mixture of 6-hydroxy-2-naphthoic acid and 3-hydroxy-2-naphthoic acid is about 0.8. The reaction mixture is then cooled to 240° C. vented to atmospheric pressure, and cooled under a nitrogen atmosphere to 120° C. Water is then added to dilute the reaction mixture.

The diluted reaction mixture is discharged into a flask containing 7.5 grams of sulfuric acid in 100 mls of water. The pH of the resulting mixture is then adjusted to 7.0±1 with sulfuric acid, and the two-phase liquid mixture is heated to 95° C. while stirring. The mixture is allowed to settle, the layers are split apart, and the aqueous phase is washed twice with 100-ml portions of isopropylnaphthalene. The isopropylnaphthalene-washed aqueous phase is then stirred at 65°–75° C. and 20 grams of a 15% by weight solution of acetic acid in water is added thereto. Sulfuric acid (15 grams of sulfuric acid per 100 mls of solution) is then added over a period of 15 to 20 minutes until the pH of the resulting slurry is 4.8 to 5.2. The slurry is then cooled to 25°–35° C. and filtered. The resulting filter cake is then washed with water and dried to obtain 21.3 grams of 6-hydroxy-2-naphthoic acid.

The aqueous mother liquor is adjusted to pH 2.5 with dilute sulfuric acid and the resulting precipitate is collected by filtration, washed, and dried to afford a recycleable stream rich in 3-hydroxy-2-naphthoic acid containing 2-naphthol dicarboxylic acid, 6-hydroxy-2-naphthoic acid and 3-hydroxy-2-naphthoic acid, wt 5.5 g.

The combined organic phases contain 63.9 grams of 2-hydroxynaphthalene, which can be recovered and recycled.

This represents a yield of 37.8%, based on KOH, and a yield of 81.2%, based on 2-naphthol.

EXAMPLE 3

A. A mixture of 2-hydroxynaphthalene (84 grams; 0.58 mole), 45% potassium hydroxide (70.5 grams; 0.56 mole), and 100 mls of a mixture of 1-, and 2-isopropylnaphthalenes is stirred and heated under a nitrogen atmosphere until 100 mls total of water and isopropylnaphthalene are distilled off. At that point, 100 mls of isopropylnaphthalene is added and the mixture is further heated to distill off an additional 50 mls of isopropylnaphthalene, and obtain a dehydrated mixture.

The dehydrated reaction mixture is cooled to 265° C., charged to a pressure reactor, and purged with carbon dioxide. The reactor is then sealed and pressurized with carbon dioxide to 40 psi while stirring slowly. The rate of stirring is then increased to 1500 rpm and the mixture is stirred at 265° C. under 40 psi of carbon dioxide for 16 hours. The reaction mixture is then cooled to 260° C. vented to atmospheric pressure, and cooled under a nitrogen atmosphere to 120° C. Water is then added to dilute the reaction mixture.

The diluted reaction mixture is discharged into a flask containing 7.5 grams of sulfuric acid in 100 mls of water. The pH of the resulting mixture is then adjusted to 7.0±1 with sulfuric acid, and the two-phase liquid mixture is heated to 95° C. while stirring. The mixture is allowed to settle, the layers are split apart, and the aqueous phase is washed twice with 100-ml portions of isopropylnaphthalene. The isopropylnaphthalene-washed aqueous phase is then stirred at 65°–75° C. and 20 grams of a 15% by weight solution of acetic acid in water is added thereto. Sulfuric acid (15 grams of sulfuric acid per 100 mls of solution) is then added over a period of 15 to 30 minutes until the pH of the resulting slurry is 4.8 to 5.2. The slurry is then cooled to 25°–35° C. and filtered. The resulting filter cake is then washed with water and dried to obtain 27.4 grams of 6-hydroxy-2-naphthoic acid.

The aqueous mother liquor is adjusted to pH 2.5 with dilute sulfuric acid and the resulting precipitate is collected by filtration, washed, and dried to afford a mixture containing 1.6 grams of 6-hydroxy-2-naphthoic acid, 2.9 grams of 3-hydroxy-2-naphthoic acid and a small amount of 2-naphthol decarboxylic acid.

The combined organic phases contain 0.2 grams of 2-hydroxynaphthalene, which can be recovered and recycled.

This represents a yield of 54% based on KOH and 62.1%, based on 2-naphthol, utilizing the most optimum conditions for a non-recycle process.

B. When the reaction of Example 3A is run in the same manner except that the temperature is 275° C., the pressure is 70 psig and the time is 8 hours, the yield on KOH is 51.4% and based on 2-naphthol is 65.4.

Thus it can be seen that the invention as described in Example 2 represents a significant increase in yield and productivity.

EXAMPLE 4

The procedure of Example 1 is again followed except that a 50/50 molar mixture of 2-hydroxynaphthalene and pure 3-hydroxy-2-naphthoic acid is used in lieu of the 2-hydroxynaphthalene alone. The presence of the 3-hydroxy-2-naphthoic acid reduces the reaction time from 4 hours to 3 hours.

EXAMPLE 5

The procedure of Example 4 is again followed except that the 3-hydroxy-2-naphthoic acid is first treated with sufficient potassium hydroxide to convert all hydroxy and carboxy groups to salts and the salts are then introduced into the dehydration step. Excellent results are achieved.

EXAMPLE 6

The procedure of Example 2 is again followed except that the 3-hydroxy-2-naphthoic acid-rich mixture is contacted with potassium hydroxide and the resultant salts are then charged to the dehydration stage. Equivalent results accrue.

EXAMPLE 7

The procedure of Example 2 is again followed except that the mixture rich in 3-hydroxy-2-naphthoic acid is replaced by the corresponding mixture from Example 3A. Again, increased production of 6-hydroxy-2-naphthoic acid based on 2-hydroxynaphthalene is realized.

EXAMPLE 8

The procedure of Example 2 is again followed except that pure 3-hydroxy-2-naphthoic acid is added to the 2-hydroxy-naphthalene-rich mixture in an amount such that the molar ratio of 2-hydroxynaphthalene to 3-hydroxy-2-naphthoic acid is about 1 to 1. Excellent results are observed.

EXAMPLE 9

The procedure of Example 8 is again followed except that the admixture of the 3-hydroxy-2-naphthoic acid rich stream and the pure 3-hydroxy-2-naphthoc acid is treated with potassium hydroxide and the resultant salts are charged to the dehydration stage of the process. Again, the results achieved are superior to those when no 3-hydroxy-2-naphthoic acid is employed.

EXAMPLE 10

Example 2 is again followed except that the flux is omitted during the carbon dioxide reaction. The results are only slightly reduced regarding product yield.

EXAMPLE 11

Example 2 is again followed except that a mixture of potassium hydroxide and potassium carbonate (3/1) is employed. Again, excellent results are obtained.

I claim:

1. In a process for preparing 6-hydroxy-2-naphthoic acid by (A) forming a mixture of 2-hydroxynaphthalene and a potassium base, (B) dehydrating the resultant mixture, (C) introducing carbon dioxide into the resultant dehydrated mixture while agitating under heat and pressure and (D) recovering 6-hydroxy-2-naphthoic acid, the improvement which comprises (E) heating said dehydrated mixture at about 270°–280° C. and about 68–74 psi until the ratio of 6-hydroxy-2-naphthoic acid to the mixture of 6-hydrox-2-naphthoic cid and 3-hydroxy-2-naphthoic acid therein is at least about 0.4 and (F) introducing 3-hydroxy-2-naphthoic acid to either step (A) or step (B).

2. The process of claim 1 wherein the 3-hydroxy-2-naphthoic acid introduced is recovered from the aqueous mother liquor resulting from the 6-hydroxy-2-naphthoic acid recovery.

3. The process of claim 2 wherein said recovered 3-hydroxy-2-naphthoic acid is introduced into step (A).

4. The process of claim 2 wherein said recovered 3-hydroxy-2-naphthoic acid is admixed with potassium base and introduced into step (B).

5. The process of claim 1 wherein the 3-hydroxy-2-naphthoic acid introduced is extraneously produced.

* * * * *